(12) United States Patent
Thiberg

(10) Patent No.: US 6,238,425 B1
(45) Date of Patent: May 29, 2001

(54) DEVICE FOR EXTERNAL MEDICAL TREATMENT WITH MONOCHROMATIC LIGHT

(75) Inventor: Rolf Thiberg, Akersberga (SE)

(73) Assignee: Biolight Patent Holding AB, Danderyd (SE)

(*) Notice: Subject to any disclaimer, the term of this patent is extended or adjusted under 35 U.S.C. 154(b) by 0 days.

(21) Appl. No.: 09/194,973
(22) PCT Filed: Jun. 4, 1997
(86) PCT No.: PCT/SE97/00977
§ 371 Date: Dec. 7, 1998
§ 102(e) Date: Dec. 7, 1998
(87) PCT Pub. No.: WO97/46279
PCT Pub. Date: Dec. 11, 1997

(30) Foreign Application Priority Data

Jun. 7, 1996 (SE) .................................................. 9602272

(51) Int. Cl.⁷ .................................................. A61N 5/00
(52) U.S. Cl. .................................. 607/88; 606/9; 606/13; 607/89
(58) Field of Search ................................. 607/88–91, 93; 606/3, 9, 10–13

(56) References Cited

U.S. PATENT DOCUMENTS

| | | | |
|---|---|---|---|
| 4,930,504 | * 6/1990 | Diamantopoulos et al. | 607/88 |
| 5,024,236 | 6/1991 | Shapiro | 128/735 |
| 5,259,380 | 11/1993 | Mendes et al. | 607/115 |
| 5,358,503 | 10/1994 | Bertwell et al. | 606/27 |
| 5,500,009 | 3/1996 | Mendes et al. | 607/88 |
| 5,766,233 | * 6/1998 | Thiberg | 607/88 |
| 5,800,479 | * 9/1998 | Thiberg | 607/88 |

FOREIGN PATENT DOCUMENTS

| | | |
|---|---|---|
| 2548354 | 5/1977 | (DE) . |
| 3134953 | 3/1983 | (DE) . |
| 0320080 | 6/1989 | (EP) . |
| 2212010 | 7/1989 | (GB) . |
| WO9118646 | 12/1991 | (WO) . |
| WO9519809 | 7/1995 | (WO) . |
| WO9519810 | 7/1995 | (WO) . |

OTHER PUBLICATIONS

"Double Blind, Placebo–Controlled Investigation of the Effect of Combined Phototherapy/Low Intensity Laser Therapy Upon Experimental Ischaemic Pain in Humans", By Basim Mokhtar et al., Laser in Surgery and Medicine, 17:74–81 (1995).

* cited by examiner

Primary Examiner—Michael Peffley
(74) Attorney, Agent, or Firm—Alfred J. Mangels

(57) ABSTRACT

Apparatus for external medical treatment with the aid of light. A light-emitting device is provided that includes light-emitting diodes or corresponding elements and is adapted to emit monochromatic light of a predetermined wavelength. The light emitting device is driven by a drive arrangement for causing the light-emitting device to emit the monochromatic light over a predetermined time and is intended to lie against or to be held in close proximity to acupuncture points on the body of an individual. The drive arrangement also is adapted to cause the light-emitting device to pulsate the light in accordance with a predetermined pulse frequency, and to cause the light-emitting device to emit the pulsating monochromatic light at a pulse repetition frequency in one of the ranges 5 Hz to 9.5 Hz, 22.2 Hz to 36.0 Hz, and 273.8 Hz to 324.0 Hz.

6 Claims, 2 Drawing Sheets

DEVICE FOR EXTERNAL MEDICAL TREATMENT WITH MONOCHROMATIC LIGHT

BACKGROUND OF THE INVENTION

1. Field of the Invention

The present invention relates to an apparatus for external medical treatment with the aid of light, and more specifically with light that will alleviate and/or cure different diseases, illnesses, sicknesses, etc., hereinafter referred generally as health disorders.

2. Description of the Related Art

The Swedish Patent Specification No. 502 784 teaches apparatus for external medical treatment with the aid of light. The apparatus includes light-emitting devices which are intended to lie against or be held in the close proximity of the body of an individual, and means for driving the light-emitting device, said light-emitting device including light-emitting diodes or corresponding light-emitting elements. According to this prior publication, the treatment apparatus also includes a drive means which functions to cause the light-emitting device to emit monochromatic light over a predetermined period of time. The drive means is also adapted to cause the light-emitting device to emit pulsating light in accordance with a predetermined series of pulse frequencies.

It has been found that apparatus of this kind can be used very successfully in the treatment of disorders and injuries, for instance injuries sustained in sporting activities, such as pulled or strained muscles, muscular pain, as well as joint pains, headaches, different inflammatory conditions, different skin complaints, such as acne, back pains, etc., provided that the light is emitted in a certain way. Treatment with light has a favorable effect on the healing of injuries and will alleviate and/or cure various health disorders.

Thus, it is realized that treatment with light in which a certain light is emitted in a certain series of frequencies will have a significantly greater effect with respect to shortening the time taken to cure or alleviate a health disorder.

SUMMARY OF THE INVENTION

The present invention is based on the conception that treatment corresponding to acupuncture treatment can be effected with the aid of emitted pulsating light that has a certain pulse frequency, wherein the light replaces conventional acupuncture needles.

The present invention thus relates to apparatus for external medical treatment with the aid of light. The apparatus includes a light-emitting device which is intended to be placed against or held in the close proximity of an acupoint on the body of an individual, and a light-emitting device drive means. The light-emitting device includes light-emitting diodes or corresponding light-emitting elements and it is adapted to emit monochromatic light of a predetermined wavelength. The drive means is adapted to cause the light-emitting device to emit monochromatic light over a predetermined period of time, and is also adapted to cause the light-emitting device to emit light that pulsates in accordance with a predetermined pulse frequency. The drive means is operative to cause the light-emitting device or elements to emit said pulsating monochromatic light at a pulse repetition frequency in one of the range 5 Hz to 9.5 Hz, 22.2 Hz to 36.0 Hz, or 273.8 Hz to 324.0 Hz.

BRIEF DESCRIPTION OF THE DRAWINGS

The invention will now be described in more detail with reference to exemplifying embodiments and also with reference to the accompanying drawings, in which.

DESCRIPTION OF THE PREFERRED EMBODIMENTS

Figure 1:
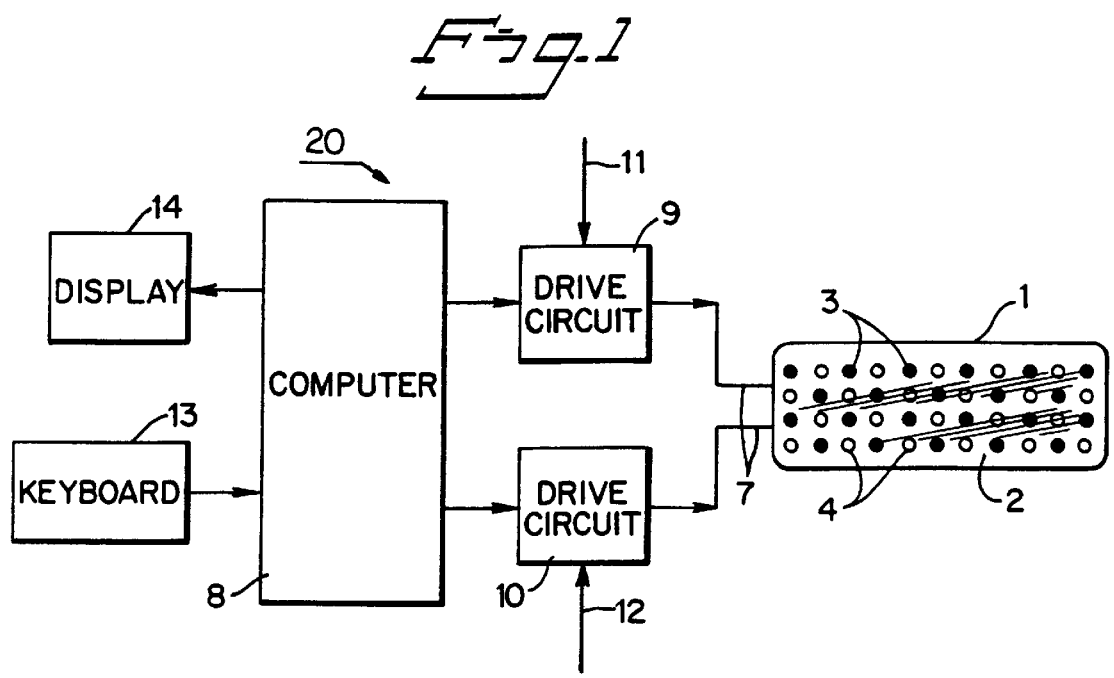
FIG. 1 is a block schematic of apparatus in accordance with the present invention for external medical treatment with the aid of light.
Figure 2:
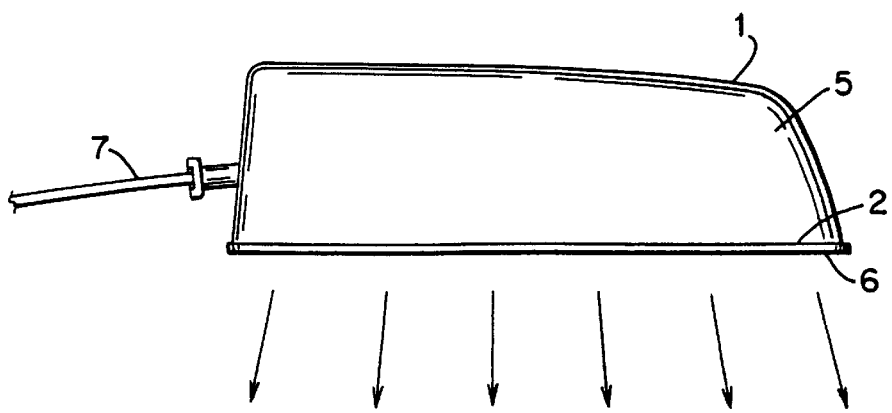
FIG. 2 is a side view of an embodiment a light-emitting device in accordance with the present invention.

FIGS. 1 and 2 illustrate one form of apparatus for external medical treatment with the aid of light. The apparatus includes a light-emitting device 1, which is intended to lie against or to be held in the close proximity of the body of an individual. FIG. 2 shows the light-emitting device from one side, while FIG. 1 shows the device from below. The light-emitting device 1 includes a housing 5 which is provided with a transparent plate 6. Located on plate 6 is a surface 2 on which a plurality of light-emitting diodes 3, 4, or corresponding light-emitting elements, are mounted. The light-emitting diodes send light through the plate 6 when the diodes are energized, i.e. supplied with current through a cable 7. In use, the housing 5 is held so that the plate 6 will lie against the part of the body to be treated. The apparatus also includes drive means 20 for driving the light-emitting device 1. The light-emitting device 1 may include light-emitting diodes, 3 or corresponding means for emitting infrared light. These diodes or the like, are shown as solid circles in FIG. 1.

The drive means 20 is adapted to cause the light-emitting device 1 to emit monochromatic light of a given wavelength over a predetermined time period. The drive means may also be adapted to emit monochromatic light of a wavelength different from the first-mentioned wavelength and over a second predetermined time period, in an optional second stage of the treatment. Visible light is emitted by light-emitting diodes 4 or corresponding elements. These diodes are shown as hollow circles in FIG. 1.

The drive means 20 is also adapted to cause the light-emitting device 1 to emit pulsating light in accordance with a predetermined pulse frequency, or a series of pulse frequencies, over predetermined time periods. The drive means 20 includes a computer 8 which functions to control drive circuits 9, 10, to which voltage is applied via conductors 11, 12 for driving the light-emitting diodes.

The computer 8 and drive circuits 9, 10 are of an appropriate known kind. Connected to the drive means 20 is a keyboard 13 by means of which the operator can enter drive means control data for actuating the light-emitting device in a desired manner. The apparatus will also conveniently include a display 14, on which the settings made through the keyboard are displayed.

Infrared light-emitting diodes 3 are preferably semiconductor diodes of the GaAs kind (Gallium arsenide). The light-emitting diodes 4 that emit visible light are also preferably of the GaAs type.

For instance, the number of light-emitting diodes included in the light-emitting device may be such that the infrared light-emitting diodes will together generate a light power of 1800 milliwatts, and the diodes that emit visible light may each have a power of 3000 millicandela.

According to one embodiment of the invention, the light-emitting device 1 includes red light emitting diodes 4 that emit visible light at the wavelength of 660 nanometers and/or infrared light emitting diodes 3 that emit light at the wavelength of 950 nanometers.

In another embodiment of the invention, the light-emitting device 1 includes light-emitting diodes 4 that emit a substantially monochromatic visible light in one of the colors violet, blue, yellow, orange, red or green.

The subject matter described above with reference to the accompanying drawings is essentially also found described in the aforementioned patent specification.

According to the invention, the drive means 20 is adapted to cause the light-emitting device or elements to emit said pulsating monochromatic light at a pulse repetition frequency in one of the ranges 5 Hz to 9.5 Hz, 22.2 Hz to 36.0 Hz, or 273.8 Hz to 324.0 Hz.

It has surprisingly been found that the inventive apparatus can be used for acupuncture treatment in a manner corresponding to acupuncture treatment with the aid of conventional acupuncture needles.

It has also surprisingly been found that the treatment, i.e. stimulation of the acupoints, is effected much more quickly than conventional acupuncture. Normally, each acupoint need only be treated for a period of about one minute, as compared with treatment for from about five minutes to up to an hour with conventional acupuncture. Furthermore, the patient need not feel any pain.

The present invention thus represents considerable steps forward in the art. Treatment is effected in the same way as conventional acupuncture, although, with the difference, that the light-emitting device is placed over the acupoint in question instead of needles, and the therapist then activates the light-emitting device such as to emit desired monochromatic light in accordance with a desired pulse repetition frequency.

Because the light-emitting device has a relatively large irradiating surface area, the acupoint in question can be found easily. It will be understood that the illuminating, or irradiating, surface area of the light-emitting device can be adapted so that a smaller surface can be made illuminating, or irradiating, for treatment at acupoints which are relatively close together, so as to avoid treating acupoints that should not be treated when treating a specific acupoint.

Three ranges of pulse repetition frequencies have been mentioned above. The intermediate range of 22.2–36.0 Hz is preferably used for so-called specific acupoints. The highest range is used for so-called weighted acupoints found on feet and hands. The lowest range is used for so-called reflex points, which are found on the ears.

The invention is not concerned with the question of which of the aforesaid monochromatic light shall best be used for different treatments. The wavelength of the light is chosen to give the intended treatment effect, depending on the health disorder or injury to be treated and also on which acupoints shall be included in the treatment.

The drive means 20 includes selector means of known kind with which the operator can choose a pulse repetition frequency that lies within each of said ranges. For instance, the selector means may include the aforesaid keyboard by means of which desired pulse repetition frequencies are set. The chosen setting will suitably be shown in the display.

Figure 3:
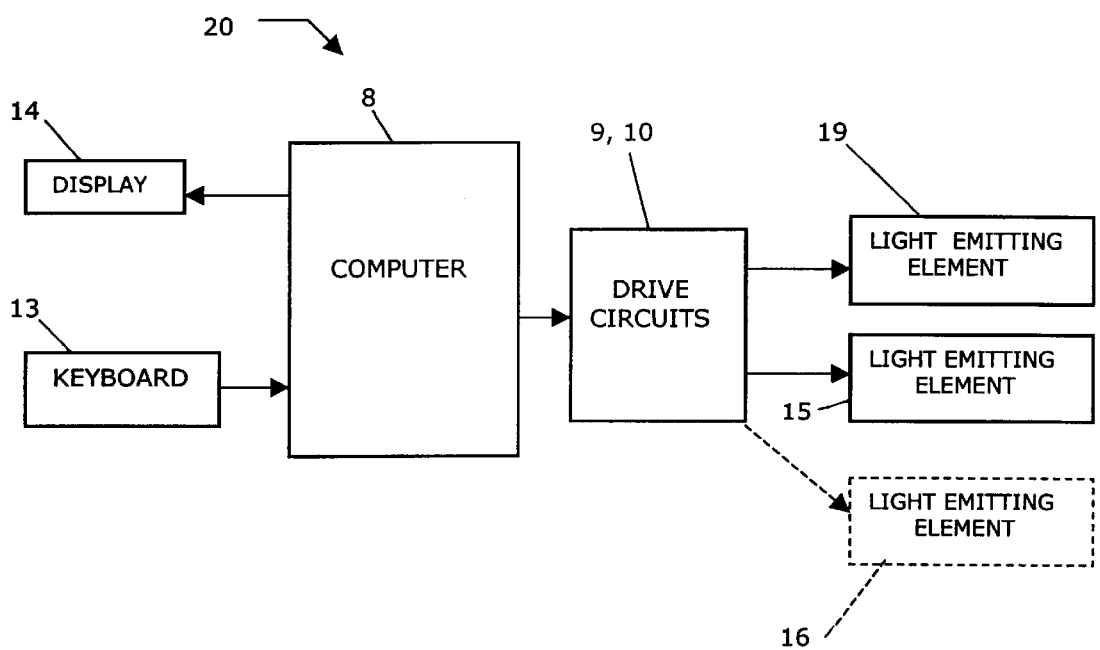
FIG. 3 illustrates another embodiment of apparatus in accordance with the present invention.

According to a preferred embodiment of the invention shown in FIG. 3, the light-emitting device 1 includes at least two separate light-emitting elements 19, 15. The separate light-emitting elements are adapted to emit monochromatic light of mutually the same wavelength. Both elements are connected to the drive means 20. When more than two light-emitting elements are included, as indicated by the light-emitting element 16 shown in broken lines in FIG. 3, all said elements are connected to the drive means 20. The drive means functions to cause each of the light-emitting elements to emit the monochromatic light synchronously in accordance with a predetermined selected pulse frequency. This embodiment thus enables two or more acupoints to be treated simultaneously.

According to one embodiment, the light-emitting device is adapted to emit monochromatic light of different wavelengths. in this case, the drive means function to cause the light-emitting device to emit solely light of one wavelength at each time point. The drive means is provided with a selector means of known kind, for instance a selector means in which the operator can enter, and therewith select, a desired wavelength, such as keyboard 13. Selected wavelengths will conveniently be shown on the display.

It will be apparent that the illustrated and described light-emitting device can be modified. For instance, the device may have the form of a light pen that emits a light point having a diameter of, e.g., 0.5 cm to 2 cm.

It will be understood that the invention is not restricted to the aforedescribed and illustrated exemplifying embodiments thereof, and that modifications and variations can be made within the scope of the following claims.

What is claimed is:

1. Apparatus for external medical treatment with the aid of light, said apparatus comprising: a light-emitting device to be held in close proximity to acupuncture points on the body of an individual, wherein the light-emitting device includes light-emitting elements that emit only monochromatic light of a predetermined wavelength at a given time, drive means for driving the light-emitting device to emit only monochromatic light of substantially only one predetermined wavelength over a predetermined period of time and to pulsate said monochromatic light of substantially only one predetermined wavelength in accordance with a predetermined pulse frequency, and selector means for setting the light-emitting device to selectively emit said pulsating monochromatic light of substantially only one predetermined wavelength at a pulse repetition frequency in one of the ranges 5 Hz to 9.5 Hz, 22.2 Hz to 36.0 Hz, or 273.8 Hz to 324.0 Hz at a given time, wherein the lowest pulse repetition frequency range is used for reflex acupoints, the intermediate range is used for specific acupoints and the highest range is used for weighted acupoints.

2. Apparatus according to claim 1, wherein the light-emitting device includes two separate, spaced light-emitting elements that are each adapted to emit monochromatic light of the same wavelength; and wherein the drive means is adapted to cause each of the light-emitting elements to emit monochromatic light synchronously in accordance with a predetermined pulse frequency.

3. Apparatus according to claim 1, wherein the light-emitting device is adapted to emit monochromatic light at different wavelengths; and wherein the drive means is adapted to cause the light-emitting device to emit light at only one wavelength at each time point.

4. Apparatus according to claim 1, wherein the light-emitting device is adapted to lie against the acupuncture points.

5. Apparatus according to claim 1, wherein the light-emitting device includes light-emitting diodes.

6. Apparatus according to claim 1, wherein the selector means includes a keyboard.

* * * * *